United States Patent [19]

Chen et al.

[11] Patent Number: 4,774,250

[45] Date of Patent: Sep. 27, 1988

[54] COMPOSITION AND METHOD FOR TREATING DIFFERENTIATED CARCINOMA OR MELANOMA CELLS WITH THIAPYRYLIUM DYES

[75] Inventors: Lan Bo Chen, Lexington, Mass.; Wilbert J. Humphlett, Rochester, N.Y.

[73] Assignee: Dana Farber Cancer Institute, Boston, Mass.

[21] Appl. No.: 33,149

[22] Filed: Apr. 2, 1987

[51] Int. Cl.⁴ .............................................. A61K 31/44
[52] U.S. Cl. .................................................... 514/336
[58] Field of Search ........................................ 514/336

[56] References Cited

U.S. PATENT DOCUMENTS

| | | | |
|---|---|---|---|
| 3,250,615 | 5/1966 | Van Allan et al. | 96/1 |
| 3,615,418 | 6/1969 | Standenmayer et al. | 96/1.5 |
| 3,679,408 | 7/1972 | Keyman et al. | 549/13 |
| 4,125,414 | 11/1978 | Tang et al. | 136/89 |
| 4,341,894 | 7/1982 | Regan et al. | 544/333 |

OTHER PUBLICATIONS

Khim-Farm., ZH., vol. 15, No. 11 pp. 38-40 (1981).
Arnold Lockshin et al., "Effectiveness of Anticancer Drugs Determined in Nude Mice Inoculated with [1251]-Iodo-2'-Deoxyuridine-Prelabeled Human Melanoma Cells", JNCI, vol. 74, No. 4, Apr. 1985, pp. 899-903.
Beppino C. Gioranella, PHD et al., "Correlation Between Response to Chemotherapy of Human Tumors in Patients and in Nude Mice"; Cancer, Oct. 1, 1983, pp. 1146-1152.

*Primary Examiner*—Jerome D. Goldberg
*Attorney, Agent, or Firm*—Dana M. Schmidt

[57] ABSTRACT

There are described an anti-cancer composition and a method of treating differentiated carcinomas or melanoma, Featuring a suitable carrier and particular 2,4,6-tri(aryl or heteroaryl) thiapyrylium dyes.

8 Claims, 3 Drawing Sheets

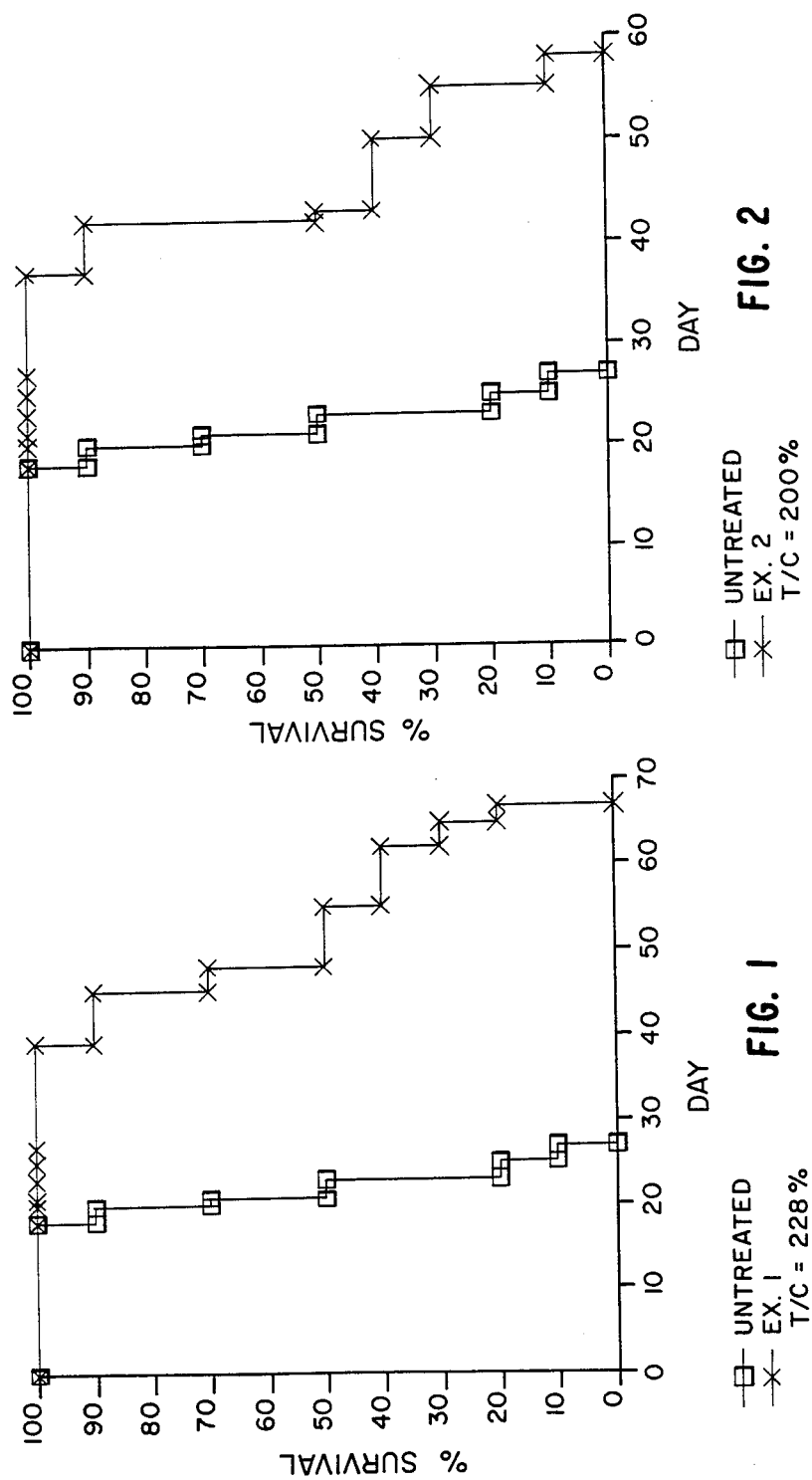

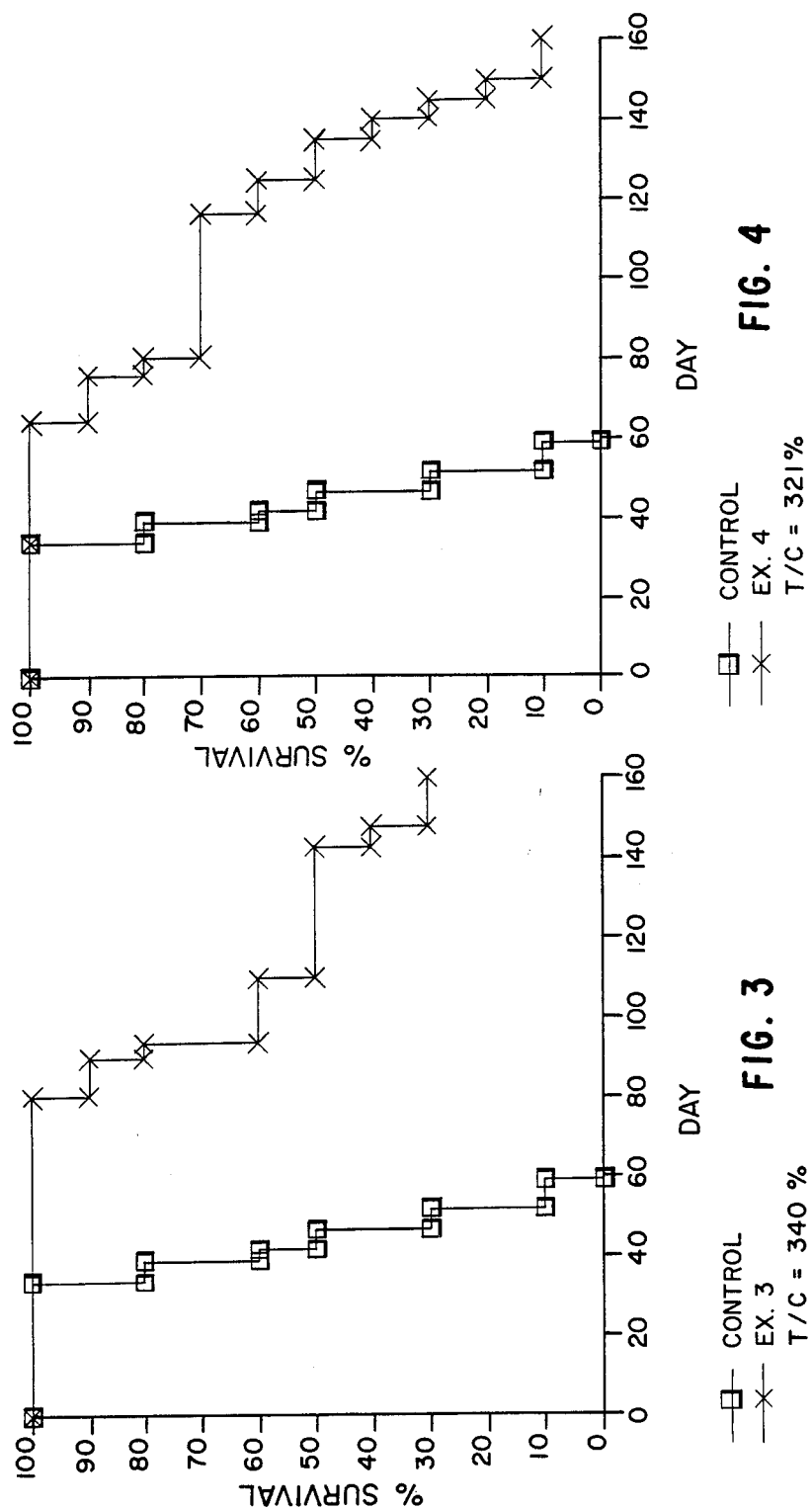

COMPOSITION AND METHOD FOR TREATING DIFFERENTIATED CARCINOMA OR MELANOMA CELLS WITH THIAPYRYLIUM DYES

FIELD OF THE INVENTION

This invention relates to a composition and a method for treating cancers involving differentiated carcinomas or melanoma.

BACKGROUND OF THE INVENTION

It is well-recognized that cancer is a scourge of the modern world, particularly of the developed nations. According to one estimate, in such countries out of a population of 100,000, up to 20,000 people can be expected to contract cancer and fail to get effective treatment. As reported in Vol. 1 of "Dynamics and Opportunities in Cancer Management" by SRI International (1985), page 6, about 5 million persons are likely to die of cancer in 1986. This is particularly devastating in view of the pain and incapacity which precedes actual death by cancer.

It is not surprising, therefore, that much attention is being given to discovering anti-tumor agents. The need for effective anti-tumor agents is so well-known that, whenever it is rumored that one has been found, the press and the public clamor for information.

One problem with conventional chemotherapeutic drugs in the treatment of cancer has been that such drugs tend to be highly toxic to healthy cells as well as to cancer cells. As a result, they produce undesirable side effects, such as alopecia (hair loss), emisis (nausea), nephrotoxicity, cardiotoxicity, etc. Another problem has been the relative lack of success when using even the most popular drugs. For example, "Adriamycin" TM, identified hereinafter, has had only a 14.5% effective response rate in treating stomach cancer in Japan, as reported in *Antibiotics Chemother.*, Vol. 24, pages 149–159 (1978).

Yet, so severe is the problem of cancer that people take such drugs and suffer such side-effects in the hope that the cancer will be alleviated before the side-effects become unbearable. There is currently available some selectivity in toxicity, that is, the ability of the chemotherapeutic agent to selectively kill carcinoma cells instead of healthy cells. However, for most such conventional chemotherapeutic agents that selectivity does not exceed 2 or 3 as defined, for example, by the $IC_{50}$ values in in vitro studies of human carcinomas. Such conventional selectivity of 2 or 3 is not adequate because undesirable side effects still plague the patient. Selectivity values defined by the $IC_{50}$ ratios of at least 5 to 1 are needed before the selectivity becomes significant enough to predict reduced undesirable side effects.

Therefore, a chemotherapeutic drug having significant selective toxicity to at least some types of cancer is a long-felt need that begs for a solution. This need particularly exists in the arena of differentiated carcinomas, since as explained in *Discover*, March, 1986, page 37, such constitute about 85% of the cancers. Such carcinomas include cancer of the so-called "hollow" organs: the breast, colon, bladder, lung, prostate, stomach and pancreas. Colon carcinomas are particularly in need of effective chemotherapeutic agents, since at present no known drug is very effective against this cancer. (*Discover*, March, 1986, pages 36–46, at page 38).

Thiapyryliums, and particularly 2,4,6-triphenylthiapyrylium perchlorates are known to have antimicrobial and anti-phage activities. These are described in e.g., *Khim-farm. ZH.*, Vol. 15, No. 11 pp. 38–40 (1981). However, there is no suggestion anywhere that these thiapyryliums will provide anti-cancer activity.

SUMMARY OF THE INVENTION

We have found that a class of thiapyrylium dyes, heretofore known primarily for their use in electrophotography, lithography and photofabrication, is effective in treating differentiated carcinomas and melanoma. The preferred members of this class of dyes are further outstanding in that they are highly selectively toxic to such carcinoma cells. Of these, the most preferred are effective against differentiated carcinoma cells at an unexpected low level of dilution. It is readily apparent that low dosage levels are preferred to avoid undesirable side-effects.

More specifically, in accord with one aspect of the invention there is provided a composition effective to treat differentiated carcinoma or melanoma cells contained in a host mammalian body, comprising a therapeutically effective amount of a thiapyrylium dye having the following structural formula:

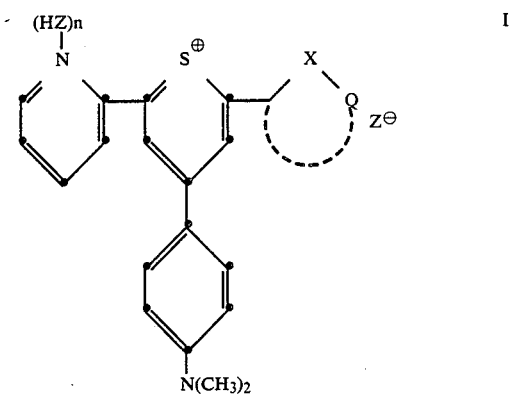

wherein X is CH or S;

Q represents the atoms necessary to complete an unsaturated carbocyclic or heterocyclic ring of 5 to 6 ring atoms;

n is 0 or 1;

and Z is a pharmaceutically acceptable anion; and a pharmaceutically suitable carrier.

In accord with another aspect of the invention, there is provided a method of treating melanoma or differentiated carcinoma cells in a host mammalian body, comprising administering to such host mammalian body having melanoma or differentiated carcinoma cancer cells, a therapeutically effective amount of the dye described above, and carrier.

Thus, it is an advantageous feature of the invention that differentiated carcinomas and melanoma are treatable in mammals using intraperitoneal (IP) administration, with a high selectivity value.

It is a related advantageous feature of the invention that such treatment occurs while minimizing undesirable side effects.

Another advantageous feature of this invention is the provision of an anti-cancer drug effective against colon carcinoma, heretofore a cancer that has been relatively immune to chemotherapeutic treatment.

Other advantageous features will become apparent upon reference to the following detailed description, when read in light of the attached drawings.

BRIEF DESCRIPTION OF THE DRAWINGS

FIGS. 1-6 are survival plots of cancer-bearing mice treated with the dyes of this invention, compared to a control group of such mice that were untreated. In these plots, "% survival" means the % of the total group (treated "T" or control "C") still surviving on the day in question. The 50% data point is selected for the T/C calculation, as being the point that is statistically meaningful.

DESCRIPTION OF THE PREFERRED EMBODIMENTS

Figure 6:
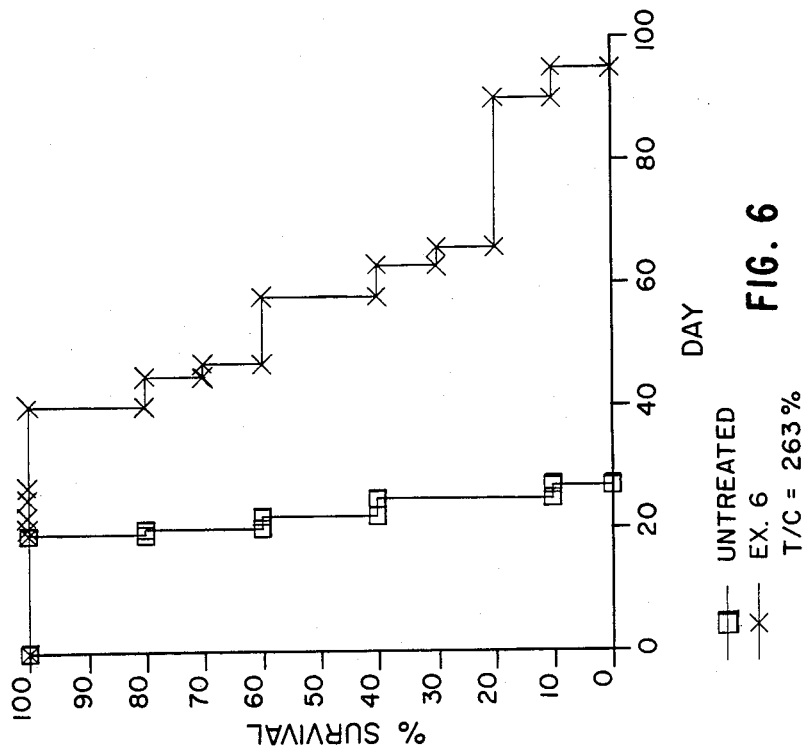

As used herein "differentiated carcinomas" includes adenocarcinomas, which include about 90% of the prostate cancers that occur in about 50% of the United States male population over 65; most squamous cell carcinomas; and all transitional cell carcinomas. The term does not include oat cell carcinoma or large cell carcinoma in the lung, or poorly differentiated carcinomas. Such carcinomas are not believed to be affected by this invention.

The effective treatment of differentiated carcinomas includes regression, palliation, inhibition of growth and remission of tumors.

Thus, the kind of specific organ cancers treatable by this invention include carcinomas of lung (except for those noted above), colon, breast, bladder, prostate, pancreas, stomach, vagina, esophagus, tongue, nasopharynx, liver, ovary, and testes.

The invention features the use of 2,4,6-tri(aryl or heteroaryl)thiapyrylium dyes as the anti-cancer agent, along with a suitable carrier.

More specifically, the preferred thiapyrylium dyes of this invention are those having the structural formula I of the Summary set forth above. In that formula, the ring formed by X and Q include, for example, thienyl and phenyl. As used herein, "pharmaceutically acceptable anion" means one that is non-toxic to the host mammal and provides an aqueous solubility to the dye of at least 0.1 mg/ml. Examples include halide such as chloride, bromide, iodide, and fluoride; sulfonate including aliphatic and aromatic sulfonate such as methanesulfonate, trifluoromethanesulfonate, p-toluenesulfonate (tosylate), naphthalenesulfonate, and 2-hydroxyethanesulfonate; sulfamate such as cyclohexanesulfamate; sulfate such as methyl sulfate and ethyl sulfate; bisulfate; borate; alkyl and dialkyl phosphate such as dimethyl phosphate, diethyl phosphate, and methyl hydrogen phosphate; pyrophosphate such as trimethylpyrophosphate and diethyl hydrogen pyrophosphate; and carboxylate, preferably carboxy- and hydroxy-substituted carboxylate. Preferred examples of carboxylate include acetate, propionate, valerate, citrate, maleate, fumarate, lactate, succinate, tartrate and benzoate.

Because they impart to the dye greater water solubility than do the other anions, the most preferred anions are the halides.

Thus, useful thiapyryliums within this class include the salts formed by any of the aforesaid anions, with the thiapyryliums listed in Table I.

The thiapyrylium dyes listed in Table I are the most preferred examples of the invention.

TABLE I

T-1: 4-(4-dimethylaminophenyl)-2-(2-pyridyl)-6-(2-thienyl)thiapyrylium chloride

T-2: 4-(4-dimethylaminophenyl)-2-phenyl-6-(2-pyridyl)thiapyrylium chloride

T-3: 4-(4-dimethylaminophenyl)-2-phenyl-6-(2-pyridyl)thiapyrylium perchlorate

T-4: 4-(4-dimethylaminophenyl)-2-(2-pyridyl)-6-(2-thienyl)thiapyrylium perchlorate Double salts of the above are also useful, and these are shown in structure I above as (HZ) bonded to the pyridinium nitrogen, where $n=1$. For example, the dichloride can be prepared by protonating the pyridinium atom with hydrochloric acid.

As noted above, one of the advantages of the invention is that the thiapyryliums described herein selectively attack the cancer cells as opposed to normal cells. Although knowledge of the mechanism is not essential to the practice of the invention, it is believed this occurs through the preferential inhibition of ATP synthesis in the mitochondria of the cancer cells. Such selectivity is further shown in clonogenic in vitro studies carried out in conventional fashion. That is, cell cultures of CX-1 (human colon carcinoma) and CV-1 (normal monkey kidney epithelial cells) are prepared and treated at various concentrations, in the conventional manner, and the concentration of the dye that inhibits 50% of the cell colonies formation is denoted as $IC_{50}$. This $IC_{50}$ value is compared for both the CX-1 and CV-1. That is, the CV-1 value is divided by the value for CX-1. If the value is 10 μg/ml for CV-1, and 1 μg/μl for CX-1, then the dye is 10 times as effective in killing off the colon carcinoma cells, compared to the monkey epithelial cells. This is expressed as a selectivity "S" of 10. That is, in order to inhibit 50% of the normal cells, the drug requires ten times the concentration needed for inhibiting 50% of the cancer cells.

The selectivity values, and the CX-1 values for four of the thiapyryliums of this invention, are listed in Table II. ("Retest" in this table refers to a repeat of the clonogenic test on either an entirely different preparation of the compound, or on a different recrystallization of the same preparation. The slight variance in selectivity can be accounted for, it is speculated, by a different moisture content in the preparation or crystallization of the compounds.)

TABLE II

| Thiapyrylium | CV-1(normal cells $IC_{50}$ value) | CX-1(colon carcinoma cells $IC_{50}$ value) | Selectivity |
|---|---|---|---|
| T-1 | 2.0 μg/ml | 0.010 μg/ml | 200 |
| T-2 | 3.0 | 0.018 | 167 |
| T-2(retest) | 0.3 | 0.005 | 60 |
| T-3 | 2.5 | 0.015 | 167 |
| T-3(retest) | 2.5 | 0.025 | 100 |
| T-4 | 5.0 | 0.015 | 333 |
| T-4(retest) | 1.5 | 0.015 | 100 |

Both the thiapyryliums of this invention and the processes for making them are well-known per se. For example, useful synthesis processes, such as the reaction of corresponding 4H-thiopyranes with a 70% perchloric acid in acetic acid, are listed in the aforesaid article in *Khim.-fram. ZH.*

The method of delivery of the dye includes implanted drug pump, intravenous (IV) intraperitoneal (IP) and intravesical injection, using a pharmaceutically acceptable carrier solvent.

The pharmaceutically acceptable carrier can be any carrier, such as a solvent that will sufficiently dissolve the thiapyrylium dye. Water alone is not considered to be a particularly good carrier solvent, although it is pharmaceutically acceptable, since many of the preferred thiapyryliums are poorly soluble in water. However, in some cases, even water may be selected if the dye can be highly dispersed, for example, by sonication, into a fine suspension. Among preferred examples of a suitable carrier solvent for human usage are a 5% dextrose solution in water, or a mixture of ethanol and a polyol such as polyethoxylated caster oil, available from the National Cancer Institute as "Diluent No. 12". Still other acceptable carrier solvents include, dimethyl sulfoxide (DMSO) for intravesical treatment; and isotonic saline for IV and IP injections.

Still other carriers that are useful include the following:

Materials such as gelatin, natural sugars such as sucrose or lactose, lecithin, pectin, starch, (for example cornstarch), alginic acid, tylose, talc, lycopodium, silica (for example colloidal silica), glucose cellulose, cellulose derivatives, for example cellulose ethers in which the cellulose hydroxyl groups are partially etherfied with lower aliphatic alcohols and/or lower saturated oxyalcohols (for example, methyl hydroxypropyl cellulose, methyl cellulose, hydroxyethyl cellulose), stearates, e.g. methyl stearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magensium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di-, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono-, or polyvalent alcohols and polyglycols such as glycorine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atoms alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate, esters of polyvalent alcohols that are etherified, benzyl benzoate, dioxolane, glycerin formal, tetrahydrofurfuryl alcohol, polyglycol ethers of 1 to 12 carbon atom alcohols, dimethyl acetamine, lactamide, lactates, e.g., ethyl lactate, ethyl carbonate, silicones (especially medium viscosity dimethyl polysiloxane), magnesium carbonate and the like.

Still other additives, and methods of preparation of the composition, can be found in the extant literature, for example, U.S. Pat. No. 4,598,091 issued on 7/1/86.

The dosage levels depend upon which thiapyrylium dye is being used on which differentiated carcinoma. Such dosage may be determined by one skilled in the art, using the techniques described in Goodman and Gilman's. "The Pharmacological Basis of Therapeutics" (6th edition), page 1675–1737, subtitled "Design and Optimization of Dosage Regimens" (Macmillan Publishing Co., New York, 1980). Based on dosages commonly experienced for chemotherapeutic agents, and the correlation that has been shown between clinical tests and the $LD_{50}$ dosages found in the nude mice protocol described hereinafter, it is estimated the dosages for human consumption would be: IV injection of 150 to 300 mg/m² every 3 weeks, 5 to 10 mg/kg daily for 4 to 8 days, or 70 to 90 mg/m² daily for 3 days or once weekly for 6 weeks. ("Mg/m²" refers to square area of the patient's body, as is customary.)

EXAMPLES

Effectiveness against human cancer can be inferred by tests in the nude mouse-human xenograft model, hereinafter "nude mice protocol". This has been suggested in, e.g., the *Journal of the National Cancer Institute*, Vol. 74, No. 4, p. 899–903, especially p. 889 (April 1985).

Nude mice, that is, those deficient in thymic functions, bred and maintained in pathogen-free conditions [See J. Natl. Cancer Inst. 51: 615–619 (1973)] were used in in vivo experiments. For each experiment, nude mice from the same litter and of the same sex which were over 3 months old and weighed at least 25 g were injected or implanted with cancer cells.

Ex. 1 & 2-Melanoma Tests Using Nude Mice Protocol

A human melanoma cell line, LOX, was used that grows rapidly when inoculated into the peritoneal cavity of athymic mice. Tumors which had been passaged subcutaneously in athymic mice were excised under sterile conditions and converted to a single cell suspension using a metal grid with a 4 mm mesh. Red blood cells were then lysed by incubation with 0.17 molar ammonium chloride at 4° C. for 20 minutes. Cells were then scored for viability with trypan blue and 5 million viable cells made up in 0.1 ml of Dulbecco modified Eagles' medium (DME) were injected intraperitoneally into a group of male athymic Swiss nu/nu mice. The mice were then randomly allocated into treatment and control groups and treatment, by intraperitoneal injection commenced the following day. Ten mice received in Ex. 1, 5 mg/kg of the drug T-2 daily for five days and 5 mg/kg three times per week thereafter (usually on Monday, Wednesday, Friday), and in Ex. 2, 10 mice received T-1 at the same dosage rate. Ten control mice received 0.25 ml of 5% dextrose on those days the treated groups were injected with drugs. The drugs tested are listed in Table IV.

TABLE IV

Generic Structure:

TABLE IV-continued

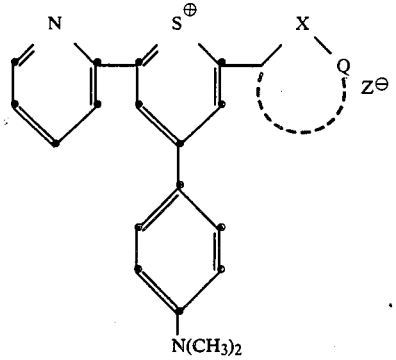

| Ex. No. | X | Q | Z |
|---|---|---|---|
| 1 | C | completes a phenyl ring | Cl |
| 2 | S | completes a thienyl ring | Cl |

The injections were administered as solutions of Ex. 1 and Ex. 2 in 5% dextrose water, made up at concentrations of 0.4 to 0.6 mg/ml.

The results of the test are shown in FIGS. 1 & 2, respectively. Specifically, 4-(4-dimethylaminophenyl)-2-phenyl-6-(2-pyridyl)thiapyrylium chloride, Ex. 1, proved to provide more than double the survival rate of the mice inoculated with melanoma cells, since T/C (or test drug versus control, calculated based on 50% survival day) was 228% (FIG. 1). In Ex. 2 (FIG. 2), T/C was 200% for 4-(4-dimethylaminophenyl)-2-(2-pyridyl)-6-(2-thienyl)thiapyrylium chloride. These are considered to be excellent demonstrations of the ability of the dye to treat the cancer and cause remission. Any T/C over 145% is generally considered to be evidence of results that are statistically significant and not explainable by experimental error or experimental variability.

Ex. 3-4 Ovarian Carcinoma (OVCAR-3) Using Nude Mice Protocol

Ex. 1 and 2 were repeated, except they were administered to female nude mice xenografted with human ovarian carcinoma line OVCAR-3. Ten mice were selected for treatment with the thiapyrylium, in an amount of 5 mg/kg administered IP 1 day after the cancer cells were injected. This was repeated as follows: daily for five days followed by twice weekly (usually on Tuesday and Thursday). Ten mice were used as the control group and were injected with 0.25 ml of 5% dextrose in water.

The results appear in FIGS. 3 & 4. The dye of Ex. 1 gave a T/C of 340%, and that of Ex. 2 gave a T/C of 321%.

Figure 5:
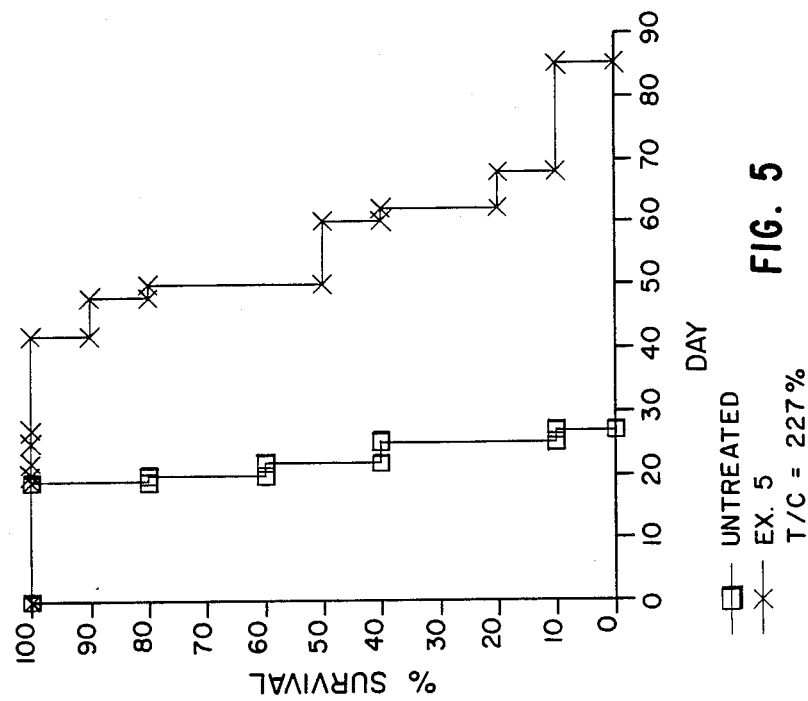

Examples 5-6-Treatment of Mouse Bladder Carcinoma Using Thiapyrylium Dyes Administered IP MB49 tumor cells, that is, mouse carcinoma cells induced by the carcinogen 7,12-dimethyl benz[a]anthracene, were injected intraperitoneally into normal male BDF1 mice ($2 \times 10^6$/mouse). Each drug treated group and control group had ten mice. Except for the control group, one of the thiapyrylium dyes of Ex. 1 and Ex. 2 was administered intraperitoneally starting the following day in the following manner: 2 mg/kg daily for 5 days followed by 2 mg/kg twice a week. The control group of 10 mice was treated with 0.25 ml of 5% dextrose in water and was the same control group used for both Ex. 5-6. The survival rate was calculated as in the previous examples. The results were that the dye of Ex. 1 produced a T/C of 227%, and the dye of Ex. 2 produced a T/C of 263%, as shown further in FIGS. 5-6.

At least part of the success of this invention in treating the carcinomas and melanoma as described above, may be attributed to inhibition of ATP synthesis, presumably through the inhibition of electron transport in the mitochondria of the cancer cells.

Comparative Examples

The following thiapyryliums were not considered acceptable, because of their selectivity "S" values in the in vitro tests discussed above, being drastically reduced compared to the selectivity values of the invention, reported in Table II above. Their generic structure is as follows:

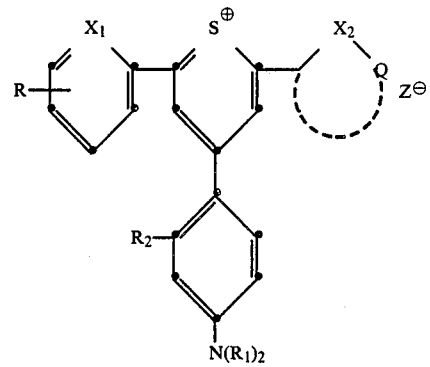

The corresponding groups and the "S" values follow in Table V.

TABLE V

| Comp. Ex. | $X_1$ | $X_2$ | Q | Z | R | $R_1$ | $R_2$ | S |
|---|---|---|---|---|---|---|---|---|
| 1 | CH | CH | completes p-methyl-phenyl group | perchlorate | methoxy | $CH_3$ | H | 2.5 |
| 2 | CH | CH | completes a phenyl group | paratoluene sulfonate | H | " | H | 5.0 |
| 3 | 2,6-Bis(2-thienyl)-4-(4-dimethylaminophenyl)thiapyrylium perchlorate | | | | | | | 1.0 |
| 4* | 4-(4-Dimethylaminophenyl)-2-(4-pyridyl)-6-(2-thienyl)thiapyrylium perchlorate | | | | | " | H | 3.3 |
| 5 | 4-(4-Dimethylaminophenyl)-2-(2-furyl)-6-(2-thienyl)thiapyrylium perchlorate | | | | | | | 13.5 |
| 6 | CH | CH | completes p-dimethyl aminophenyl | "paratoluene sulfonate | H | " | H | 10.0 |

TABLE V-continued

| Comp. Ex. | $X_1$ | $X_2$ | Q | Z | R | $R_1$ | $R_2$ | S |
|---|---|---|---|---|---|---|---|---|
| 7 | CH | CH | completes phenyl | " sulfonate | H | $(CH_2)_2Cl$ | $CH_3$ | <7.5 |
| 8 | CH | CH | completes phenyl | paratoluene sulfonate | H | benzyl | H | <7.5 |
| 9 | CH | CH | completes phenyl | tetrafluoroborate | H | $(CH_2)_2Cl$ | H | <5.0 |
| 10** | CH | CH | completes phenyl | chloride | H | $CH_3$ | H | 5.0 |

*Compare with T-4 in Table II.
**Compare with T-2 in Table II.

The invention has been described in detail with particular reference to preferred embodiments thereof, but it will be understood that variations and modifications can be effected within the spirit and scope of the invention.

What is claimed is:

1. An injectable pharmacological composition effective to treat differentiated carcinoma or melanoma cells contained in a host mammalian body, comprising an amount of a thiapyrylium dye sufficient to produce inhibition of growth or remission of said carcinoma or melanoma, said dye having the following structural formula:

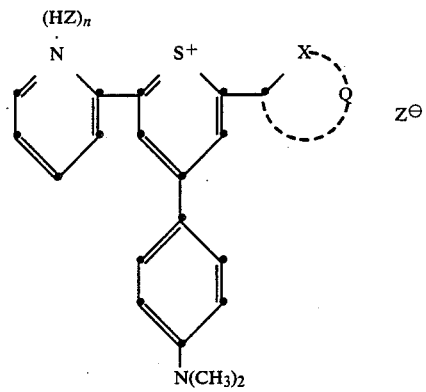

wherein X is CH or S;
Q represents the atoms necessary to complete an unsaturated carbocyclic or heterocyclic ring of 5 to 6 ring atoms;
n is 0 or 1;
and Z is a pharmaceutically acceptable anion;
and a pharmaceutically suitable carrier.

2. A composition as defined in claim 1, wherein said dye is 4-(4-dimethylaminophenyl)-2-(2-pyridyl)-6-(2-thienyl)thiapyrylium chloride.

3. A composition as defined in claim 1, wherein said dye is 4-(4-dimethylaminophenyl)-2-phenyl-6-(2-pyridyl)thiapyrylium chloride.

4. A method of treating differentiated carcinoma or melanoma cells in a host mammalian body, comprising administering by injection to said host mammalian body having differentiated carcinoma or melanoma cancer cells, an amount of a thiapyrylium dye sufficient to produce inhibition of growth or remission of said carcinoma or melanoma, said dye having the following structural formula:

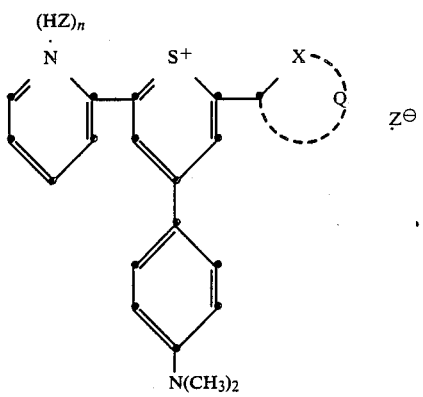

wherein X is CH or S;
Q represents the atoms necessary to complete an unsaturated carbocyclic or heterocyclic ring of 5 to 6 ring atoms;
n is 0 or 1;
and Z is a pharmaceutically acceptable anion;
and a pharmaceutically suitable carrier.

5. A method as defined in claim 4, wherein said dye is 4-(4-dimethylaminophenyl)-2-(2-pyridyl)-6-(2-thienyl)-thiapyrylium chloride.

6. A method as defined in claim 4, wherein said dye is 4-(4-dimethylaminophenyl)-2-phenyl-6-(2-pyridyl)-thiapyrylium chloride.

7. A method as defined in claim 4, wherein said carcinoma is selected from the group consisting of carcinoma of the lung, colon, breast, bladder, prostate, pancreas, stomach, vagina, esophagus, tongue, nasopharynx, liver, ovary and testes.

8. A method as defined in claim 4, wherein said effective amount is 150 to 300 mg/m² every 3 weeks, 5 to 10 mg/kg daily for 4 to 8 days, or 70 to 90 mg/m² daily for 3 days or once weekly for 6 weeks, administered by IV.

* * * * *